(12) United States Patent
Waddell et al.

(10) Patent No.: US 8,564,924 B1
(45) Date of Patent: *Oct. 22, 2013

(54) SYSTEMS AND METHODS OF AIR TREATMENT USING BIPOLAR IONIZATION

(75) Inventors: Charles Houston Waddell, Roanoke, VA (US); Joseph Christiansen, Savannah, GA (US)

(73) Assignee: Global Plasma Solutions, LLC, Savannah, GA (US)

( * ) Notice: Subject to any disclaimer, the term of this patent is extended or adjusted under 35 U.S.C. 154(b) by 987 days.

This patent is subject to a terminal disclaimer.

(21) Appl. No.: 12/578,753

(22) Filed: Oct. 14, 2009

Related U.S. Application Data

(60) Provisional application No. 61/105,110, filed on Oct. 14, 2008, provisional application No. 61/221,763, filed on Jun. 30, 2009.

(51) Int. Cl.
*H01T 23/00* (2006.01)
(52) U.S. Cl.
USPC .......................................................... 361/231
(58) Field of Classification Search
USPC .......................................................... 361/231
See application file for complete search history.

(56) References Cited

U.S. PATENT DOCUMENTS

| | | |
|---|---|---|
| 3,744,216 A | 7/1973 | Halloran |
| 3,804,942 A | 4/1974 | Kato et al. |
| 3,956,458 A | 5/1976 | Anderson |
| 4,048,668 A | 9/1977 | Von Bargen et al. |
| 4,244,710 A | 1/1981 | Burger |
| 4,308,844 A | 1/1982 | Persinger |
| 4,417,966 A | 11/1983 | Krauss et al. |
| 4,519,357 A | 5/1985 | McAllister |
| 4,538,582 A | 9/1985 | Wakuta |
| 4,597,781 A | 7/1986 | Spector |
| 4,809,127 A | 2/1989 | Steinman et al. |
| 4,828,586 A | 5/1989 | Joannou |
| 4,886,526 A | 12/1989 | Joannou |
| 4,901,194 A | 2/1990 | Steinman et al. |
| 4,951,172 A | 8/1990 | Steinman et al. |
| 5,010,869 A | 4/1991 | Lee |
| 5,055,115 A | 10/1991 | Yikai et al. |
| 5,055,963 A | 10/1991 | Partridge |
| 5,108,470 A | 4/1992 | Pick |
| 5,185,015 A | 2/1993 | Searle |
| 5,474,599 A | 12/1995 | Cheney et al. |
| 5,486,410 A | 1/1996 | Groeger et al. |
| 5,487,874 A | 1/1996 | Gibboney, Jr. |
| 5,573,577 A | 11/1996 | Joannou |
| 5,616,172 A | 4/1997 | Tuckerman et al. |
| 5,656,063 A | 8/1997 | Hsu |
| 5,681,374 A | 10/1997 | Von Glehn |

(Continued)

OTHER PUBLICATIONS http://atmosair.wordpress.com/category/bi-polar-ionization; Oct. 28, 2010; 6 pgs.

*Primary Examiner* — Stephen W Jackson
(74) *Attorney, Agent, or Firm* — Clements Bernard PLLC; Seth L. Hudson

(57) ABSTRACT

A system and method of treating air. Bipolar ionization is delivered to an airflow within a conduit from a tubeless ion generator. The ionized airflow may be delivered to a conditioned airspace by an HVAC system. In alternate applications, the airflow delivers ionized combustion air to an engine. The invention also includes a mounting assembly for positioning one or more ion generators into an airflow.

4 Claims, 7 Drawing Sheets

(56) References Cited

U.S. PATENT DOCUMENTS

| | | |
|---|---|---|
| 5,702,507 A | 12/1997 | Wang |
| 5,707,429 A | 1/1998 | Lewis |
| 5,807,425 A | 9/1998 | Gibbs |
| 5,837,207 A | 11/1998 | Summers |
| 5,846,302 A | 12/1998 | Putro |
| 5,950,424 A | 9/1999 | Nojima |
| 5,977,716 A | 11/1999 | Motouchi |
| 6,002,573 A | 12/1999 | Partridge |
| 6,036,738 A | 3/2000 | Shanbrom |
| 6,053,968 A | 4/2000 | Miller |
| 6,058,698 A | 5/2000 | Coral et al. |
| 6,063,167 A | 5/2000 | Rutkowski |
| 6,090,184 A | 7/2000 | Cartellone |
| 6,118,645 A | 9/2000 | Partridge |
| 6,149,717 A | 11/2000 | Satyapal et al. |
| 6,322,614 B1 | 11/2001 | Tillmans |
| 6,463,917 B1 | 10/2002 | Silver |
| 6,471,752 B1 | 10/2002 | Lewis |
| 6,536,418 B1 | 3/2003 | Ling |
| 6,601,570 B2 | 8/2003 | Zetmeir |
| 6,610,123 B2 | 8/2003 | Wu et al. |
| 6,693,788 B1 | 2/2004 | Partridge |
| 6,752,970 B2 | 6/2004 | Schwartz et al. |
| 6,764,533 B2 | 7/2004 | Lobiondo, Jr. |
| 6,785,114 B2 | 8/2004 | Gorczyca et al. |
| 6,805,732 B1 | 10/2004 | Billiotte et al. |
| 6,850,403 B1 | 2/2005 | Gefter et al. |
| 7,132,010 B2 * | 11/2006 | Carlsson ............ 96/55 |
| 7,177,133 B2 | 2/2007 | Riskin |
| 7,258,729 B1 | 8/2007 | Barsimanto et al. |
| 7,311,752 B2 | 12/2007 | Tepper et al. |
| 7,341,049 B2 | 3/2008 | Clack |
| 7,347,888 B2 | 3/2008 | Hecker et al. |
| 7,368,003 B2 | 5/2008 | Crasper et al. |
| 7,384,619 B2 | 6/2008 | Bar-Gadda |
| 7,407,624 B2 * | 8/2008 | Cumberland et al. .......... 422/28 |
| 7,475,656 B2 | 1/2009 | Yatsenko |
| 7,691,335 B2 | 4/2010 | Park et al. |
| 7,749,313 B2 | 7/2010 | Byon et al. |
| 7,858,054 B2 | 12/2010 | Manalo |
| 7,906,080 B1 * | 3/2011 | Botvinnik ................ 422/186.04 |
| 2005/0123436 A1 | 6/2005 | Cumberland |
| 2005/0142047 A1 | 6/2005 | Baik et al. |
| 2008/0274012 A1 | 11/2008 | Cumberland et al. |
| 2010/0008010 A1 | 1/2010 | Orihara et al. |
| 2010/0018398 A1 | 1/2010 | Krell et al. |
| 2010/0175391 A1 | 7/2010 | Jee et al. |
| 2010/0247389 A1 | 9/2010 | Abate |
| 2010/0251889 A1 | 10/2010 | Haruna et al. |

* cited by examiner

US 8,564,924 B1

SYSTEMS AND METHODS OF AIR TREATMENT USING BIPOLAR IONIZATION

CROSS-REFERENCE TO RELATED APPLICATIONS

This application claims the benefit of U.S. Provisional Patent Application Ser. No. 61/105,110 filed Oct. 14, 2008, and U.S. Provisional Patent Application Ser. No. 61/221,763 filed Jun. 30, 2009, the entireties of which are hereby incorporated herein by reference.

TECHNICAL FIELD

The present invention relates generally to the field of air treatment, and more particularly to the treatment of air using bipolar ionization.

BACKGROUND

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

In automotive and other engine applications, combustion air is filtered and mixed with fuel for delivery to the engine intake. Combustion air is also filtered and delivered to the intake of oil and gas burners, for example in heating and electrical generation applications.

Needs exist for improved systems and methods of treating and delivering air for these and other applications. It is to the provision of improved systems and methods meeting these needs that the present invention is primarily directed.

SUMMARY

In example embodiments, the present invention provides improved systems and methods of treating and delivering air, for example in HVAC and combustion air applications, through the application of bipolar ionization to an airflow. In representative forms, the invention may improve efficiency and performance, for example providing improved fuel mileage, greater power output, reduced emissions, reduced particulates, and/or other benefits.

In one aspect, the present invention relates to a system for treatment of an airflow within a conduit. The system includes at least one bipolar ion generator having first and second electrodes, the first electrode generating positive ions and the second electrode generating negative ions. The first and second electrodes are aligned generally perpendicular to the airflow within the conduit whereby at least a portion of the positive ions and the negative ions do not recombine within the airflow.

In another aspect, the invention relates to a combustion system including a combustion air intake for delivering combustion air along a flowpath; and at least one bipolar ion generator for delivering positive and negative ions into the combustion air. Each bipolar ion generator has positive and negative electrodes, the positive and negative electrodes being aligned generally crosswise relative to the flowpath of the combustion air.

In still another aspect, the invention relates to an HVAC system including a shared outdoor heat exchanger and a plurality of individual air handler unit housings connected to the shared outdoor heat exchanger for delivery of individual airflows through each of the individual air handler unit housings. The system further includes at least one tubeless bipolar ion generator for delivering ions to the individual airflows through each of the individual air handler unit housings.

In another aspect, the invention relates to a method of treatment of an airflow within a conduit. The method includes the steps of providing at least one bipolar ion generator having first and second electrodes for delivery of positive and negative ions within the conduit, and aligning the first and second electrodes generally perpendicularly to the airflow within the conduit whereby at least a portion of the positive ions and the negative ions do not recombine within the airflow.

In another aspect, the invention relates to a mounting assembly for application of bipolar ionization to an airflow within a conduit. The mounting assembly preferably includes an enclosure for mounting to the conduit, and an arm extending from the enclosure for extension into the conduit. At least one ion generator is coupled to the arm, the ion generator having a pair of electrodes and being positioned on the arm such that an axis extending between the electrodes is oriented generally perpendicular to a flow direction of the airflow within the conduit.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1A:
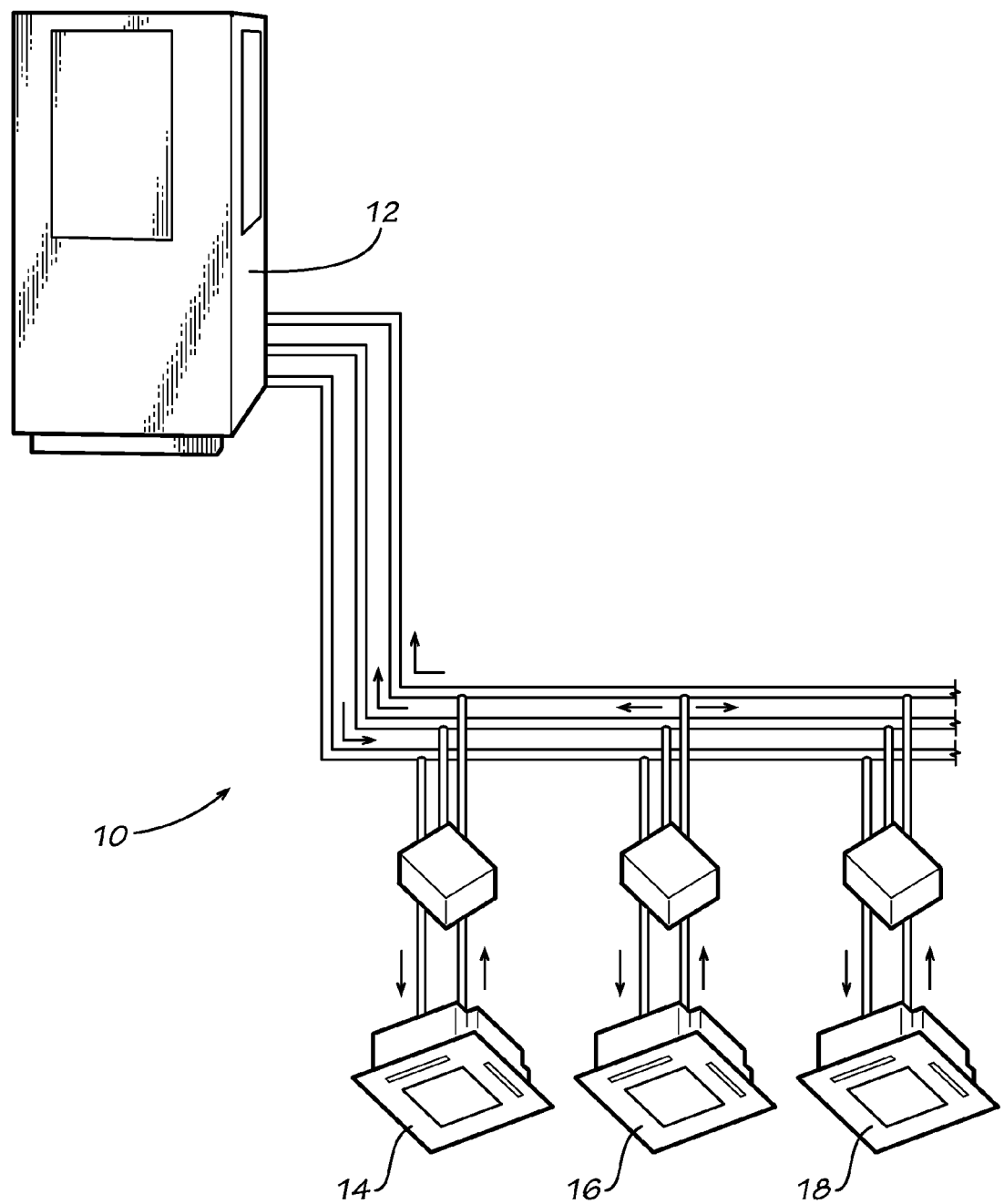
FIG. 1a is a schematic view of an HVAC system for delivering bipolar ionization to an airflow according to an example form of the present invention.

With reference now to the drawing figures, wherein like reference numbers represent corresponding parts throughout the several views, FIG. 1a shows an HVAC system 10 according to one example form of the invention. In the depicted embodiment, the HVAC system is a variable refrigerant volume (VRV) system having a shared outdoor heat exchanger 12 and a plurality of individual air handler units 14, 16, 18. In alternate forms of the invention, the HVAC system can take the form of a variable air volume (VAV), constant air volume (CAV), variable refrigerant flow (VRF) or other forms of heating, ventilation and air conditioning system.

In typical fashion, the shared outdoor heat exchanger 12 comprises a condenser coil, compressor and fan; the individual air handler units 14, 16, 18 each comprise a fan, expansion valve, heating/cooling coil(s), and a filter; and refrigerant lines connect the shared outdoor heat exchanger to the individual air handler units. Return air from the conditioned space and/or fresh air from an exterior space is treated and delivered to a conditioned air space via the individual air handler units 14, 16, 18. The outdoor heat exchanger 12 discharges waste heat from the conditioned air space to the ambient surroundings, and/or transfers heat from a cooled zone to a heated zone.

Figure 1B:
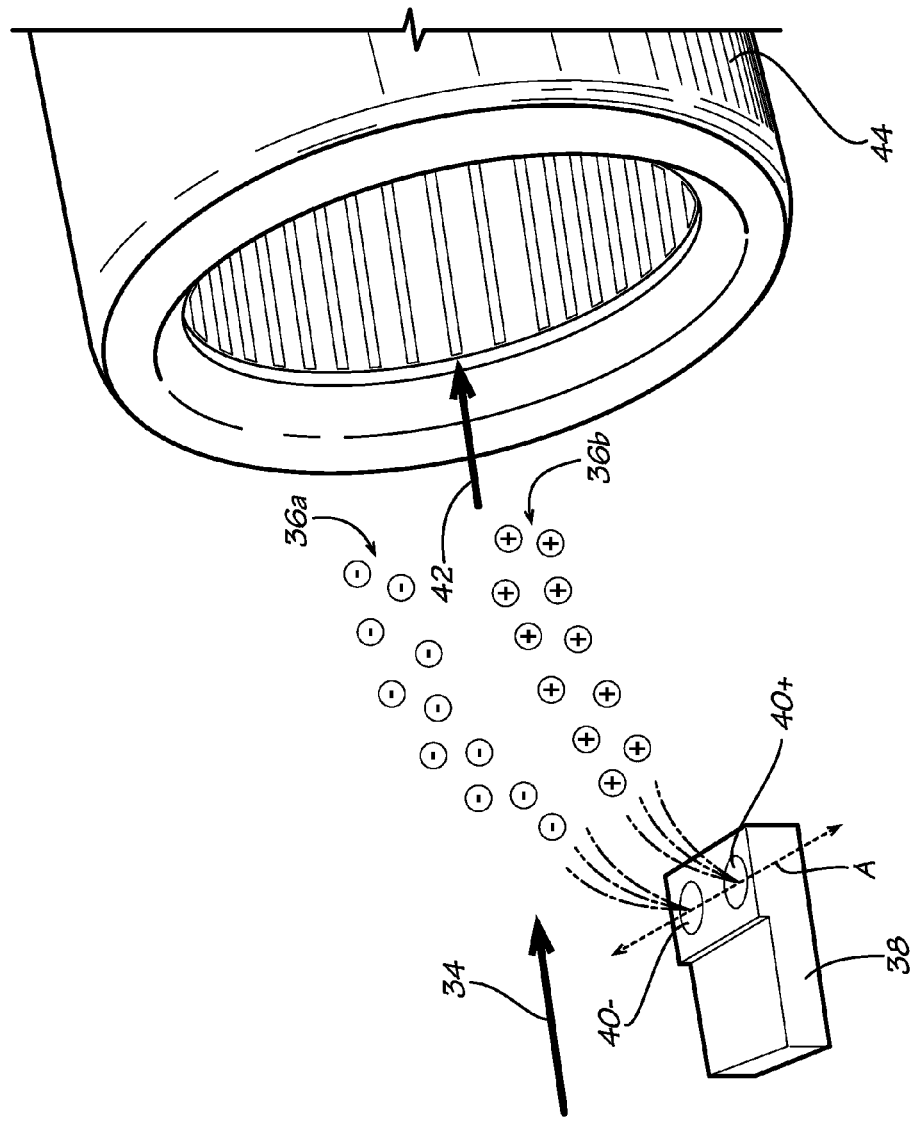
FIG. 1b is a detailed view of a portion of an air handler component of an HVAC system according to an example form of the present invention.

FIG. 1b shows internal components of an individual air handler unit according to an example form of the invention. An inlet airflow 30 flowing through a conduit such as the housing of the air handler unit or a duct is filtered through a filter 32 such as a mesh, screen, paper, cloth or other filter media. A filtered airflow 34 downstream of the filter 32 is treated by discharge of bipolar ionization 36 from an ion generator 38 to form an ionized airflow 42. The bipolar ionization 36 comprises a stream of negatively charged (−) ions 36a, and a stream of positively charged (+) ions 36b. The ionized airflow 42 enters the inlet of a fan or blower 44 for delivery to the treated air space, and is optionally heated or cooled by passing across or through a cooling coil or heating element. The coil, filter 32, ion generator 38 and fan 44 are optionally mounted within a housing of the air handler unit. Example modes of attachment of the ion generator include, without limitation, adhesive, hook-and-loop fasteners, straps, screws, clips or other mechanical fasteners, magnetic mounting, and/or mounting brackets or carriers affixed to or through the housing or associated ductwork.

The bipolar ion generator 38 is preferably a tubeless ion generator and comprises at least one pair of air ionizing needlepoint electrodes 40$^+$ (positive ion generation) and 40$^-$ (negative ion generation) such as for example needles of stainless steel, carbon fiber, tungsten, steel or other metal; and optionally further comprising onboard control circuitry. The ion generator preferably produces approximately equal amounts of positive and negative ions, regardless of airflow velocity or other conditions such as humidity or temperature. U.S. Pat. No. 7,177,133, hereby incorporated herein by reference, discloses an example form of ion generator, although it will be understood that various different ion generators may be adapted for use in connection with the present invention, including for example, the Sterionizer™ ion generator sold by Filt Air Ltd. of Zikhron Yaaqov, Israel. In example forms, each ion generator 38 produces positive and negative ions in a concentration of at least about $10^9$ ions/second, and operates on 12V DC, 110V AC, or other power source. In alternate embodiments, the ion generator(s) generate negative ions only, or positive ions only, or generate negative and positive ions in unequal quantities. The ion generator optionally utilizes nano-electronic components allowing the ion generator to be very compact, requiring less than 1 watt/ion generator module, for example less than 0.5 watts/ion module, and in further examples less than 0.36 watts per ion module. In example forms, the ion generator produces minimal or no ozone, for example at no greater concentration than in ambient air. Wiring may be routed through the housing for connection to an external power source, and a power inverter may be included to convert the source voltage to the required input voltage of the ion generator. Optionally, the ion generator automatically controls the ion discharge output based on preset algorithms, setpoints or other criteria, which may vary in relation to the airflow rate across the electrodes.

The bipolar ion generator 38 is positioned and secured in place within the housing of the air handler unit such that the electrodes 40$^+$ and 40$^-$ are aligned generally perpendicularly to the direction of the airflow 34 across the ion generator, to prevent recombination of the positively charged ions with the negatively charged ions. In other words, a vector representing the average flow velocity of the airflow 34 is at approximately a right angle ($90^2$) to an axis A extending between the electrodes 40$^+$ and 40$^-$. One or more ion generator(s) 38 can be installed within the housing of each air handler unit, as required to generate the desired level of ion delivery for a given airflow, as may be determined by the airflow rate (CFM) of the fan 44 and ion discharge rate of each ion generator. The ion generator(s) are preferably positioned generally centrally in relation to the airflow or evenly distributed across the airflow path. If more than one ion generator is provided in an air handler unit, they are sufficiently spaced and positioned relative to one another to minimize recombination of positive ions with negative ions.

The system of the present invention optionally further comprises the application of ultraviolet (UV) light, and/or a catalyst such as for example TiO$_2$ for initiating photo-catalytic oxidation, in combination with ion generation, for abating allergens, pathogens, odors, gases, volatile organic compounds, bacteria, virus, mold, dander, fungus, dust mites, animal and smoke odors, and/or static electricity in a treated air space.

Figure 2A:
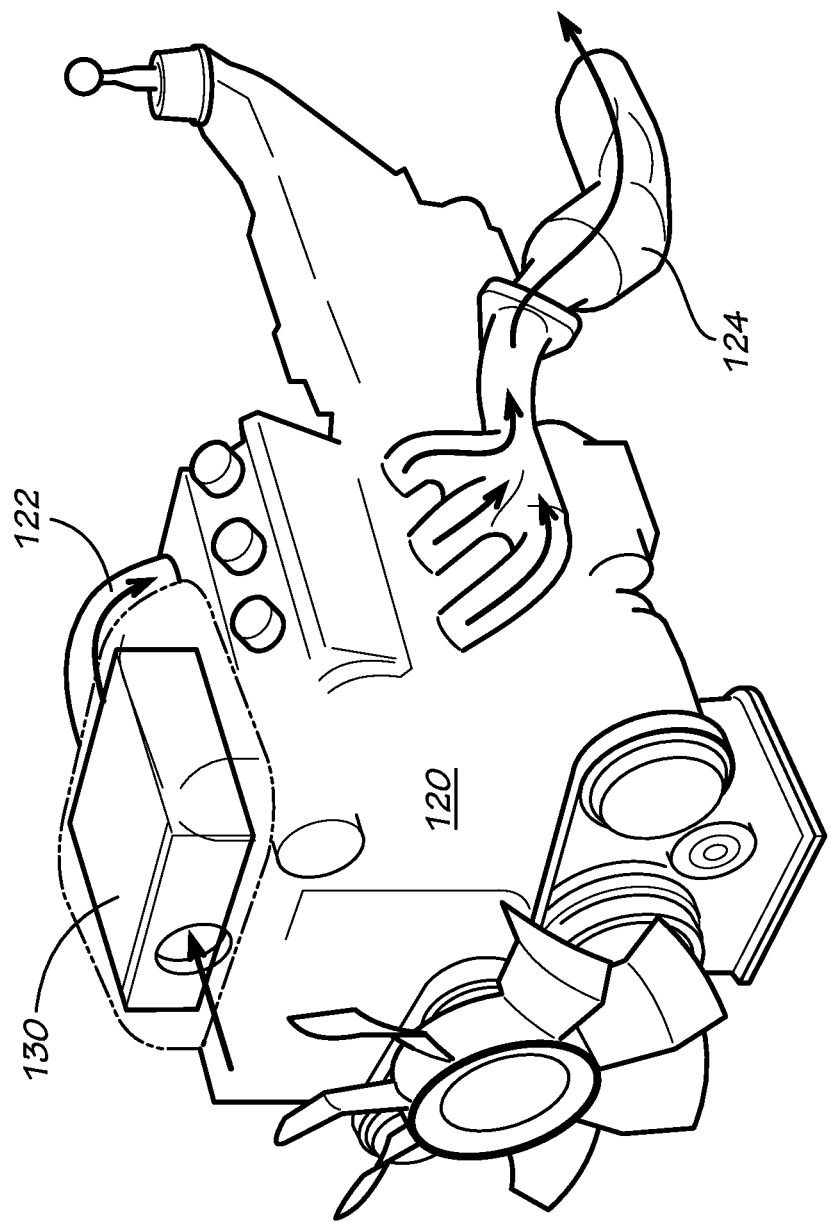
FIG. 2a shows a system for delivering bipolar ionization to an airflow within an internal combustion engine according to another example form of the present invention.
Figure 2B:
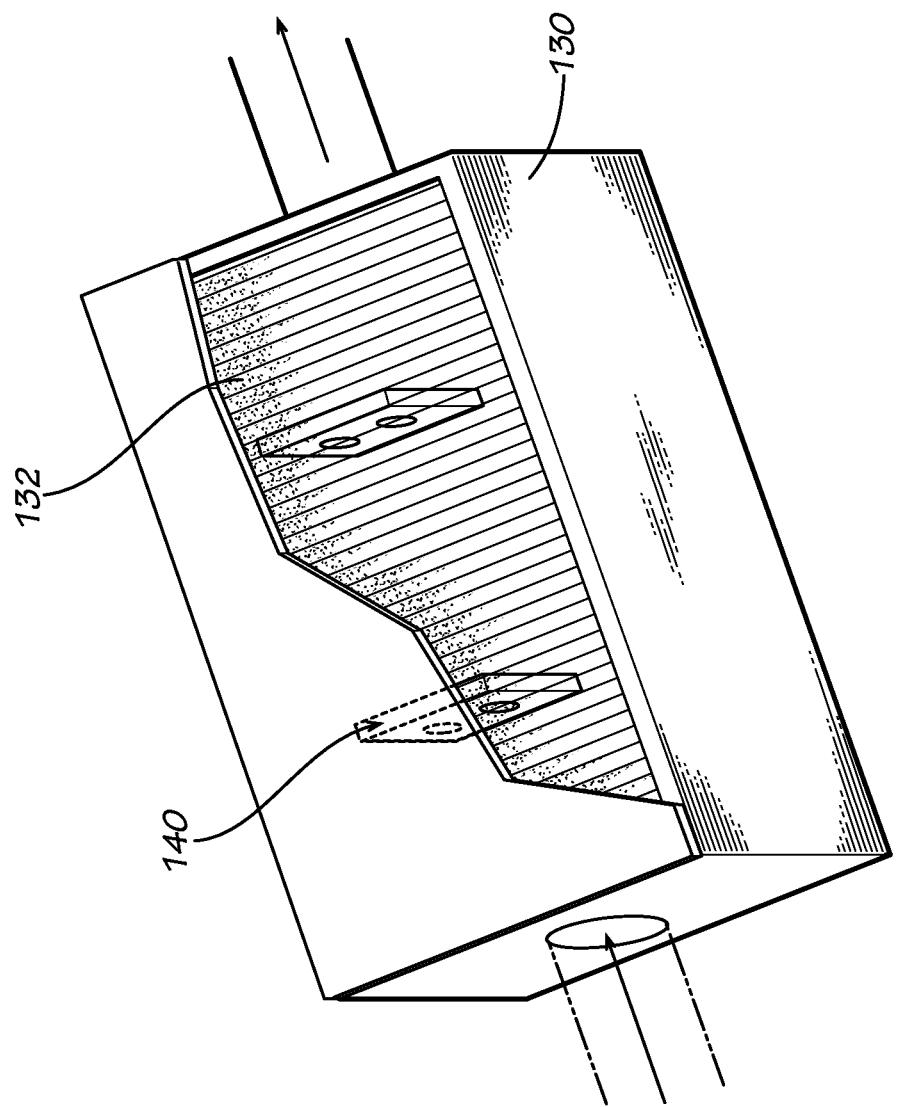
FIG. 2b is a detailed view of a filter housing portion of the system of FIG. 2a according to an example form of the present invention.

FIGS. 2a and 2b show another system 110 for treating and delivering air according to the present invention, in this embodiment comprising an internal combustion engine 120. The system 110 includes an air intake conduit 122 containing an intake airflow and an exhaust conduit 124 containing an exhaust airflow. A filter housing 130 is positioned within the air intake conduit 122, and houses an air filter 132 in typical fashion. The filter 132 comprises paper, non-woven material, or other filter media, and includes a series of pleats to provide an increased surface area for removal of particulate matter from the airflow.

One or more bipolar ion generators 140, for example as described above, are positioned within the filter housing 130, for example mounted to the housing or retained between pleats of the filter 132, for delivery of bipolar ionization to the intake air delivered for mixture with fuel and combustion in the engine. The provision of a tubeless needlepoint electrode ion generator operating on 12V DC advantageously enables ease of retrofit and/or original equipment application, and connection via wiring to the electrical system of a vehicle driven by the engine 120, preferably via a fused connection. As in the above-described embodiment, the electrodes of the ion generator 140 are aligned generally perpendicularly to the airflow to prevent ion recombination. If multiple ion generators are provided, the electrodes are sufficiently spaced and positioned to maintain the positive ion discharge unaligned with the negative ion discharge, for example by orienting the electrodes of different ion generators facing away from one another along the discharge side of the air filter 132. One or more brackets or mounts are optionally provided for attachment of the system to the engine or other combustion gas delivery component.

The treatment of air by delivery of bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

Application of bipolar ionization to an airflow conduit in automotive applications such as the intake to or exhaust from the engine may be utilized for removing particulates from the intake or exhaust flows, improving combustion efficiency, increasing the intake flowrate of combustion gas, increasing fuel mileage and/or performance, and/or reducing emissions. For example, application of bipolar ionization to the intake air of an engine at a delivery rate of about $10^9$ ions/second or greater may break down water ($H_2O$) vapor in the intake air through electrolysis and create elevated levels of oxygen ($O_2$) and hydrogen ($H_2$) in the air delivered to the engine for combustion. The provision of highly ionized intake air that is denser in $O_2$ and $H_2$ content than incoming ambient air results in longer and/or hotter combustion of fuel, increasing cylinder pressure and creating more torque and horsepower for the same percentage of throttle and fuel consumption. Optionally, the water content of the intake air may be increased, for example by injection into the intake air stream from an external source of water such as a remote tank or the condensate from a vehicle's air conditioner, to further enhance the generation of oxygen and hydrogen by ionization.

Ionization of the engine exhaust gasses, for example via a venturi inlet that draws cool ionized air into the exhaust flow, may effectively eliminate the need for a catalytic converter by agglomerating unburned carbon particulates to prevent their becoming airborne, and by dissociating undesirable emission constituents (for example dissociating $NO_X$ into $N_2$ and $O_2$, dissociating $SO_X$ into $S_2$ and $O_2$, dissociating CO into C and $O_2$, etc.). In this aspect, the system and method of the present invention may be particularly advantageous in diesel engine applications, as well as in gasoline engine applications and other engine types.

Other applications within the scope of the invention may similarly improve combustion performance by delivery of bipolar ionization to the intake air delivered to heating boilers, gas-fired heaters, electrical power generation boilers, water heaters, locomotives, and/or other combustion devices. Water vapor molecules present in or added to the intake air may be dissociated by application of bipolar ionization into $H^+$, $OH^+$, $H^-$ and $OH^-$ ions, OH, H, O, and/or $HO_2$.

Figure 3A:
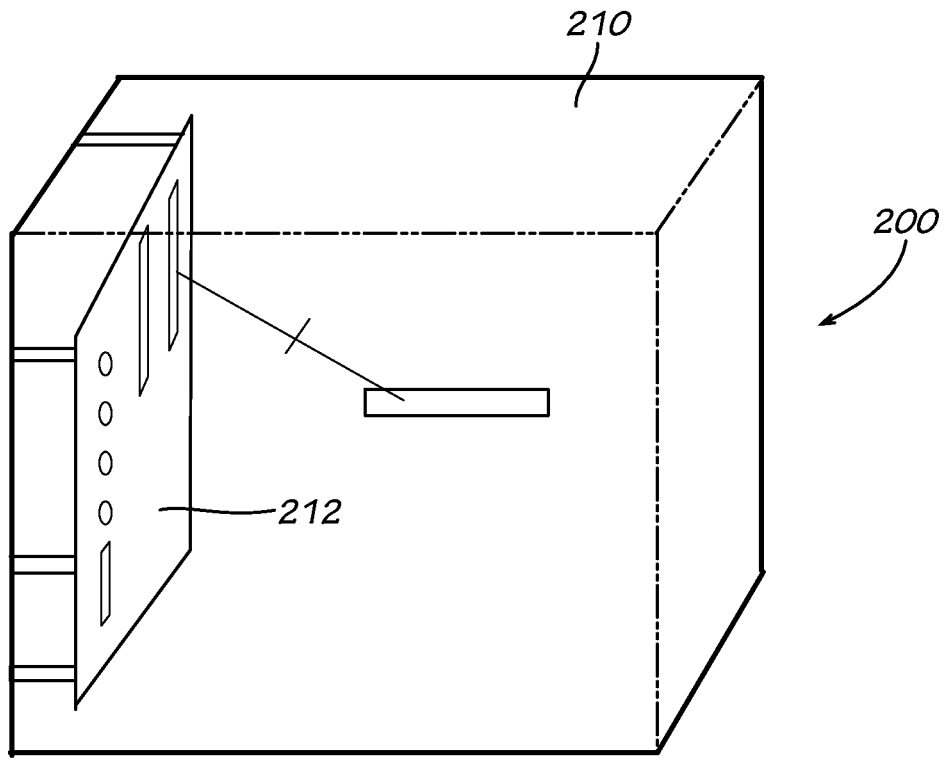
FIG. 3 shows an ion generator control module and mounting assembly according to an example form of the present invention.
Figure 3B:
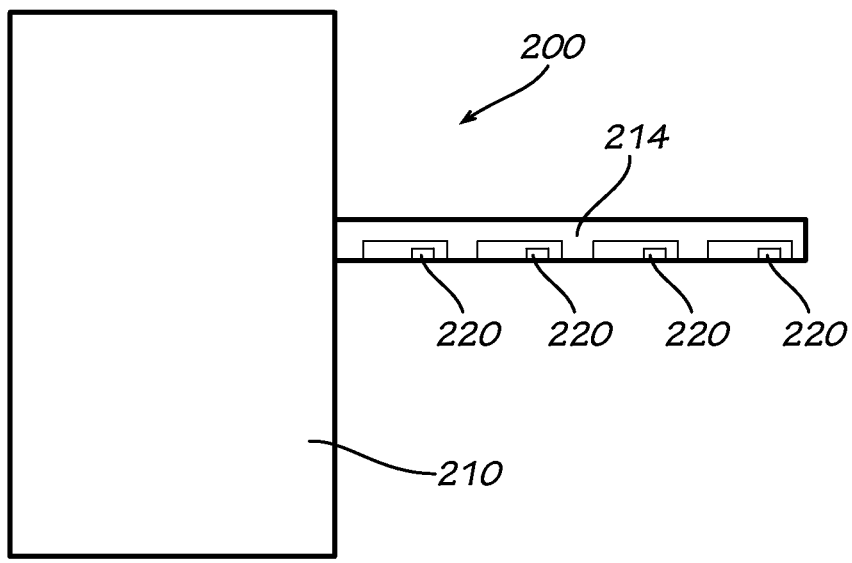

The present invention also includes a number of ion generator carrier and mounting assemblies for application and control of delivery of bipolar ionization to an airflow. FIGS. 3a and 3b show an example embodiment of an assembly 200 for mounting to the exterior of a duct, housing, or other conduit for an airflow. The assembly includes a box 210 or other enclosure, such as for example a NEMA 4x enclosure or similar configuration, an internal panel 212 within the box, and an external arm 214 projecting from the back side of the box. The external arm 214 includes mountings and electrical contacts for receiving one or more (four are depicted) bipolar ion generators 220 for delivery of bipolar ionization to an airflow within the conduit. The mountings securely engage the ion generators 220 and maintain them in an orientation having their electrodes axially aligned with the arm 214 and generally perpendicular to the airflow. The panel 212 optionally comprises one or more pluggable terminal blocks for wiring connection to the ion generators via the contacts on the arm 214, a connection for power input, and one or more indicators such as LEDs to indicate the presence/absence and operational state (on/off, ion output, etc.) of the ion generators. Optionally, a power converter or transformer is provided in the box 210 for converting the input power to the power required to operate the ion generators. One or more connectors are optionally provided for mounting the box 210 to the exterior of a duct or housing, with the arm 214 extending into the duct or housing through an opening formed therein. Sealing means such as a gasket are optionally provided on the back of the box 210 around the arm 214 for sealing around the opening.

Figure 4:
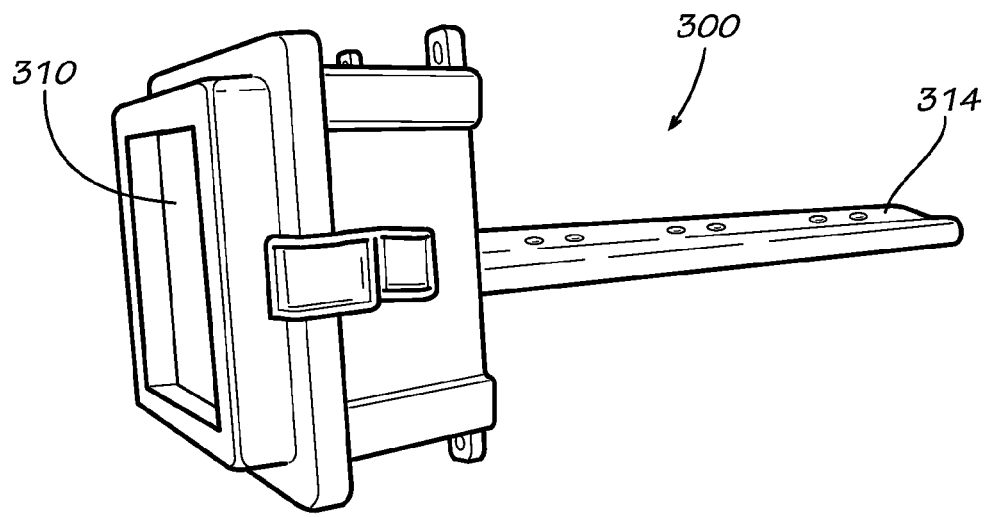
FIG. 4 shows a bipolar ion generator mounting assembly and delivery module according to an example form of the present invention.

FIG. 4 shows an assembly 300 according to an alternate embodiment, having a reclosable box 310 with an arm 314 extending therefrom, and otherwise being substantially similar to assembly 200. The length of the arm 214 may vary depending on the size of the conduit it is to be applied to and the number of ion generators to be installed, and in example embodiments is between 2"-24", for example about 10" in length.

Figure 5:
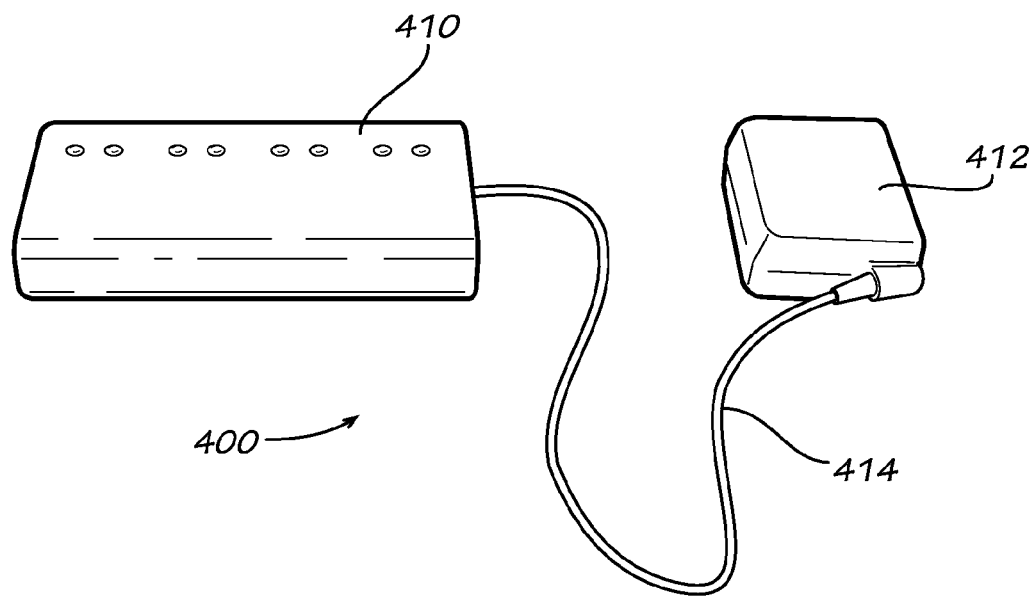
FIG. 5 shows a bipolar ion generator mounting assembly and delivery module according to another example form of the present invention.

FIG. 5 show another embodiment of an ion generator mounting assembly 400 according to the present invention. The assembly 400 includes an external power supply 410 for mounting external of the duct, housing or other conduit; and one or more ion generators 412 for mounting internal of the conduit for delivery of bipolar ionization to an airflow within the conduit. Wires 414 extending between the external power supply 410 and the ion generators 412 pass through an opening in the wall of the conduit to deliver power from the power supply to the ion generators. The external power supply 410 optionally comprises control circuitry and/or indicators for displaying the operational state of the ion generators.

Figure 6:
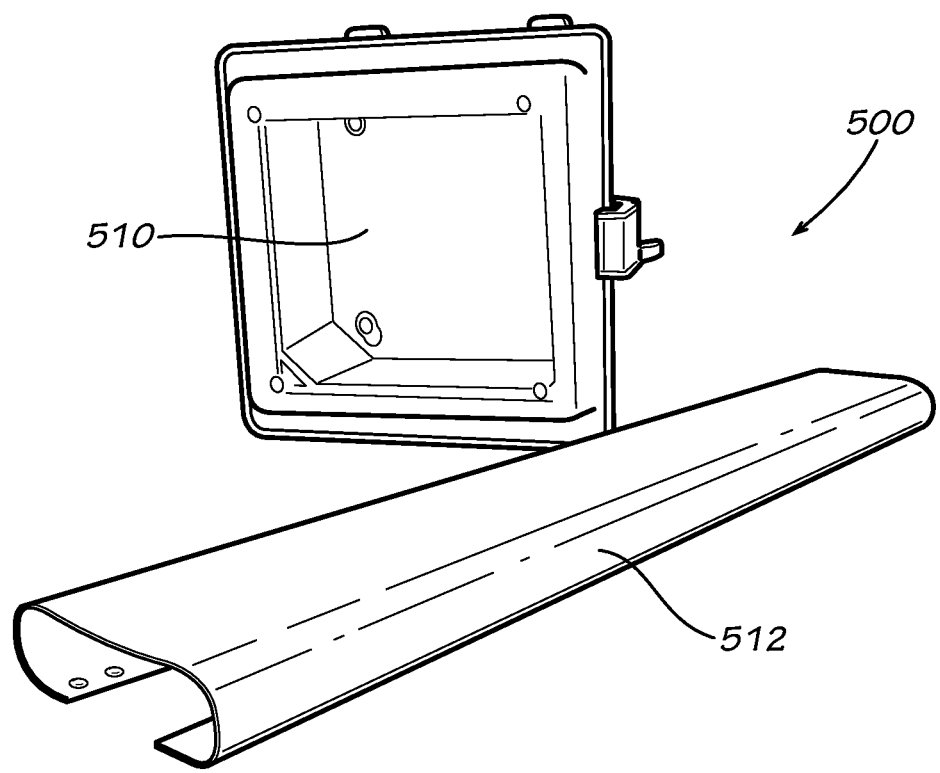
FIG. 6 shows a bipolar ion generator mounting assembly and delivery module according to another example form of the present invention.

FIG. 6 shows another embodiment of an ion generator mounting assembly 500 according to the present invention. The assembly 500 includes a control panel 510 for mounting external of the duct, housing or other conduit, and an internal rack 512 for mounting in the conduit's interior. The rack 512 includes electrical couplings and mounting receivers for receiving at least one, and preferably a plurality of ion generators for delivery of bipolar ionization to an airflow within the conduit.

While the invention has been described with reference to preferred and example embodiments, it will be understood by those skilled in the art that a variety of modifications, additions and deletions are within the scope of the invention, as defined by the following claims.

What is claimed is:

1. An ion generator mounting assembly for application of bipolar ionization to an airflow within a conduit, the mounting assembly comprising:
    an enclosure for mounting to the conduit having an internal panel within the enclosure;
    an arm extending from the enclosure for extension into the conduit; and
    at least one coupling for mounting an ion generator to the arm oriented with an axis extending between a pair of electrodes of the ion generator being generally perpendicular to a flow direction of the airflow within the conduit.

2. The ion generator mounting assembly of claim 1, wherein the coupling comprises electrical contacts on the arm for delivering power to the at least one ion generator.

3. The ion generator mounting assembly of claim 1, further comprising at least one terminal block for wiring connection to the ion generators via contacts on the arm.

4. The ion generator mounting assembly of claim 1, further comprising a power converter for converting input power to operate the ion generators.

* * * * *